(12) United States Patent
Tam

(10) Patent No.: US 6,324,245 B1
(45) Date of Patent: Nov. 27, 2001

(54) METHOD AND APPARATUS FOR IDENTIFYING AND CORRECTING IMAGE INACCURACIES CAUSED BY SIMPLIFIED PROCESSING OF MASKED CONE BEAM PROJECTION DATA

(75) Inventor: Kwok Tam, Edison, NJ (US)

(73) Assignee: Siemens Corporation Research, Inc., Princeton, NJ (US)

(*) Notice: Subject to any disclaimer, the term of this patent is extended or adjusted under 35 U.S.C. 154(b) by 0 days.

(21) Appl. No.: 09/690,630

(22) Filed: Oct. 17, 2000

(51) Int. Cl.⁷ .................................................. A61B 6/63
(52) U.S. Cl. .................. 378/4; 378/15; 378/901
(58) Field of Search ............... 378/4, 8, 15, 901; 382/131

(56) References Cited

U.S. PATENT DOCUMENTS

| | | | |
|---|---|---|---|
| 5,881,123 | * | 3/1999 | Tam .......... 378/4 |
| 6,018,561 | * | 1/2000 | Tam .......... 378/4 |
| 6,084,937 | * | 7/2000 | Tam et al. ....... 378/4 |

* cited by examiner

Primary Examiner—Drew Dunn
(74) Attorney, Agent, or Firm—Donald B. Paschburg

(57) ABSTRACT

A method and apparatus for three dimensional (3D) computerized tomographic (CT) imaging of an object, wherein image reconstruction processing is applied to a plurality of sets of 2D cone beam projection data, each set being acquired on a 2D detector at a corresponding plurality of scan path source positions. A first image reconstruction processing step comprises applying a mask to each set of the projection data so that data inside the boundaries of each mask form a corresponding plurality of masked 2D data sets. Next, the data inside each masked 2D data set is processed along line segments formed in the masked 2D data set, and having their endpoints determined by the mask boundaries, to develop a first 2D estimate of data determined from a given set of the 2D cone beam projection data. The next step comprises identifying portions of said line segments which is not used to develop said first 2D estimate of data, to develop 2D correction data for each of the first 2D estimates of data. The final step comprises combining each of the first estimates of data and the 2D correction data calculated therefore, in a process which reconstructs an exact 3D image of the object.

13 Claims, 4 Drawing Sheets

METHOD AND APPARATUS FOR IDENTIFYING AND CORRECTING IMAGE INACCURACIES CAUSED BY SIMPLIFIED PROCESSING OF MASKED CONE BEAM PROJECTION DATA

CROSS-REFERENCE TO RELATED APPLICATIONS

This application includes subject matter related to U.S. patent application entitled A Method and Apparatus for Simplifying the Correction of Image Inaccuracies Caused by Processing of Masked Cone Beam Projection Data, filed simultaneously herewith by the present inventor.

BACKGROUND OF THE INVENTION

1. Field of the Invention

The invention relates generally to a cone beam computed tomography (CT) imaging system, and more specifically to a method and apparatus for identifying and correcting image inaccuracies caused by simplified processing of masked cone beam projection data.

2. Description of the Prior Art

Recently a system employing cone beam geometry has been developed for three-dimensional (3D) computed tomography (CT) imaging that includes a cone beam x-ray source and a 2D area detector. An object to be imaged is scanned, preferably over a 360° angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

As well known, and fully described for example in the present inventor's U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, incorporated herein by reference, image reconstruction processing generally begins by calculating Radon derivative data from the acquired cone beam data. The Radon derivative data is typically determined by calculating line integral derivatives for a plurality of line segments L drawn in the acquired cone beam data. In the embodiment described in detail in the U.S. Pat. No. 5,257,183, Radon space driven conversion of the derivative data is used to develop an exact image reconstruction of a region-of-interest (ROI) in the object. Calculation of the line integral derivative data is a relatively complex and computationally time consuming task.

A cone beam data masking technique is known which improves the efficiency of the calculation of the derivative data in such Radon space driven reconstruction processing, as described in the present inventor's U.S. Pat. No. 5,504,792 entitled METHOD AND SYSTEM FOR MASKING CONE BEAM PROJECTION DATA GENERATED FROM EITHER A REGION OF INTEREST HELICAL SCAN OR A HELICAL SCAN, issued Apr. 2, 1996, also incorporated herein by reference. The masking technique facilitates efficient 3D CT imaging when only the ROI in the object is to be imaged, as is normally the case. In the preferred embodiment described therein, a scanning trajectory is provided about the object, the trajectory including first and second scanning circles positioned proximate the top and bottom edges, respectively, of the ROI, and a spiral scanning path connected therebetween. The scanning trajectory is then sampled at a plurality of source positions where cone beam energy is emitted toward the ROI. After passing through the ROI, the residual energy at each of the source positions is acquired on an area detector as a given one of a plurality of sets of cone beam data. Each set of the cone beam data is then masked so as to remove a portion of the cone beam data that is outside a given sub-section of a projection of the ROI in the object and to retain cone beam projection data that is within the given sub-section. The shape of each mask for a given set of cone beam data is determined by a projection onto the detector of the scan path which is above and below the source position which acquired the given set of cone beam data. The masked (i.e., retained) cone beam data is then processed so as to develop line integral derivative reconstruction data. An exact image of the ROI is developed by combining the reconstruction data from the various source positions which intersect a common integration plane. Hence, the masks are commonly referred to as "data-combination" masks.

Although the use of the data combination masks significantly reduces the processing required in Radon driven approaches, calculation of the line integral derivative data is still a relatively complex task and computationally time consuming. One known technique for developing the line integral derivative reconstruction data in such a Radon space driven reconstruction processing approach, is to use linograms. Although the linogram technique provides for a much faster and more simplified processing of the masked data for developing the line integral derivative reconstruction data, its creates less than exact, i.e., quasi-exact, reconstructed images.

Data-combination masks can also be used to improve the efficiency of the calculation of the derivative data in detector data driven techniques, such as those using Filtered Back-Projection (FBP) techniques. A "simplified" FBP technique is described in the present inventor's U.S. Pat. No. 5,881,123 entitled SIMPLIFIED CONE BEAM IMAGE RECONSTRUCTION USING 3D BACKPROJECTION, issued Mar. 9, 1999, also incorporated herein by reference. This simplified technique reconstructs the image using 2D approximation data sets formed by ramp filtering of the masked cone beam data. The filtering is carried out in the direction of the projection of a line drawn tangent to the scan path at the source position that acquired that set of cone beam data. Although this technique is also less complex than the prior techniques, the reconstructed image is also quasi-exact.

Accordingly, the present inventor's U.S. Pat. No. 6,084,937 entitled ADAPTIVE MASK BOUNDARY CORRECTION IN A CONE BEAM IMAGING SYSTEM, issued Jul. 4, 2000, and also incorporated herein by reference, describes a technique for computing 2D correction data which, when combined with the ramp filtered 2D approximation data sets, is intended to yield an exact image reconstruction. The 2D correction data basically comprises a point spread function representative of image reconstruction processing for each point on the detector which intersects the boundary of the data-combination mask.

Although this technique, as well as the technique of the forenoted U.S. Pat. No. 5,504,792 are intended to yield and exact image reconstruction, the present inventor has realized that such techniques are in fact also quasi-exact. More specifically, in an exemplary filtered backprojection (FBP) image reconstruction, on a detector let u and v be the Cartesian coordinate axes of the detector with the v axis coinciding with the rotation axis, and let $L(\theta,s)$ denote the line on which projection/backprojection is carried out, where $(\theta-\pi/2)$ is the angle line $L(\theta,s)$ makes with the u axis, and s is the displacement of the line from the origin. Filtering of the cone beam image consists, either explicitly or implicitly, of the combined operation $D_t H$, where $D_t$ is the differentiation (spatial) operation in the projected scan path direction t, and H is a shorthand notation for $\int B(\theta) D_s(\theta) P(\theta) d\theta$. $P(\theta)$ is the 2D projection operation (line integration) at angle $\theta$, $D_s(\theta)$ is the 1D differentiation operation with respect to s for the projection at angle $\theta$, and $B(\theta)$ the 2D backprojection operation at angle $\theta$.

FIGS. 1A and 1B illustrate this combined operation in an FBP reconstruction processing technique, such as described in the forenoted U.S. Pat. No. 6,084,937. FBP image reconstruction consists of two different kinds of processing: the first kind is 2-dimensional (2D) and the second kind is 3-dimensional (3D). In the 2D step each cone beam projection image is processed in a 2D space, and in the 3D step the processed 2D images are backprojected into a 3D object space. The 2D step consists of the following 4 FBP image reconstruction sub-steps for processing the cone beam data acquired at each of a plurality of the source positions ($S_i$) along the scan path:

1. Compute a 1D projection (i.e., a line integral) of the cone beam image acquired on a detector plane 100, at each of a plurality of angles $\theta$. This step is illustrated in FIG. 1A for a given angle $\theta_1$ of a plurality of angles $\theta$. A 1D projection 102 is shown at coordinates s, $\theta_1$ comprising the integrated values of the cone beam image 104 on detector plane 100 along a plurality of parallel lines L(s, $\theta$) that are normal to angle $\theta_1$, each line L being at an incremental distance s from an origin O. As shown and described below in conjunction with FIGS. 2 and 3 illustrating the concept and implementation of data combination, the lengths of the lines L will be limited using the forenoted masking techniques. Generally, if the detector plane 100 comprises an N by N array of pixels, then the number of angles $\theta$ is typically given by $\pi N/2$.

2. Filter (differentiate) each 1D projection 102 in accordance with a d/ds filter, resulting in a new set of values at each of the s, $\theta$ coordinates, such as shown by the derivative projection 106 for the angle $\theta_1$ shown in FIG. 1A. Note, the sum (integration) of the resulting values at these s, $\theta$ coordinates yield a quantity proportional to the Radon derivative for an integration plane Q(s, $\theta$), as described above for Radon space driven image reconstruction processing.

3. As illustrated by FIG. 1B, backproject the derivative projection 106 from each angle $\theta$ into a 2D object space 107 (which coincides with the detector plane 100). Lines 108 are representative of this backprojection, and spread the value from each s coordinate into 2D space 107 in a direction normal to each $\theta$, thereby developing contributions to a backprojection image 109. Note, 2D object space 107 has a size corresponding to a virtual detector which is enlarged (compared with detector having a height corresponding to the pitch of the scan path), so as to cover an entire region of interest (ROI in the object. This enlargement is required because the calculated Radon data affects the reconstruction of the entire Q plane, and not just the partial plane represented by the data combination mask.

4. Perform a 1D d/dt filtering of the backprojection image formed in 2D space 107 by step 3. The 1D filtering is performed in the direction of the scan path, i.e., along lines 110, where t points in the direction of the projection of a line drawn tangent to the scan path.

In a further "simplified" FBP reconstruction processing technique, the above steps 1–3 are combined into a single step of "Feldkamp" ramp filtering of the masked 2D projection data in the t (projection of a tangent to the scan path) direction, as described in detail in the present inventor's forenoted U.S. Pat. No. 5,881,123.

After step 4 above, and as shown in FIG. 1B, the 3D step comprises performing a weighted 3D backprojection of the thus filtered data from 2D space 107 (i.e., from each pixel in the detector) onto a plurality of sample points P in a 3D object volume 112. The density assigned to each point P is weighted by the inverse of the square of the distance between the sample point and the location of the x-ray.

Common in image reconstruction techniques using a data combination mask, such as in the above described FBP and simplified FBP techniques, is the forenoted data combination masking process for limiting the x-ray coverage of the integration plane at each source position to the angular range bounded by the prior source position below and the subsequent source position above the current source position. Such data combination from several source positions which intersect a common integration (Q) plane is illustrated in FIG. 2. More specifically, FIG. 2 represents a typical integration plane Q(s, $\theta$) intersecting a cylindrical object and a spiral scan path, which is assumed to wrap around the object on an imaginary cylinder and having top and bottom circular scan paths even with top and bottom edges of a region-of-interest (ROI) in the object. An edge view of plane Q is illustrated in FIG. 4 (described in the detailed portion of the description). Since a non-vertical plane will intersect a cylinder in an ellipse, the plane Q(s, $\theta$) intersects the object and the cylindrical spiral scan path in two ellipses, E1 and E2, respectively, one inside the other, as shown in FIG. 2.

Since the spiral path lies on the scan path cylinder, it intersects the plane Q in points that lie on the ellipse E2. These source positions are shown as S1, S2, and S3 in FIG. 2. Similarly, it is easy to see that the top scan path circle intersects the plane in two points T1 and T2 which lie at the intersection between E2 and the top edge of the object's ROI and that the bottom circle intersects the plane in the two points B1 and B2 which lie at the intersection between E2 and the bottom edge of the object's ROI. Other integration planes may have more or less spiral scan path intersections, depending upon their orientation, and may not intersect either of the top or the bottom circle scan paths.

As is apparent from FIG. 2, the source positions which illuminate that portion of integration plane Q that lies within the ROI are $T_2$, $S_1$, $S_2$, $S_3$, and $B_2$. Complete X-ray coverage of region-of-interest 200 of this portion of the integration plane can be achieved by suitably combining the data acquired at these 5 source positions, as indicated in FIG. 3. For example, at $T_2$ we only use the cone beam data within the angle bound by $T_1 T_2$ and $T_2 S_1$, and at $S_1$ we only use the cone beam data within the angle bound by $T_2 S_1$ and $S_1 S_2$.

And so on. Five partial planes P1 through P5 are therefore defined by the source positions $T_2$, $S_1$, $S_2$, $S_3$, and $B_2$, which do not overlap and together completely cover the portion of plane Q that lies within the ROI. In this way the totality of the cone beam data from each of the contributing source positions illuminates the entire Q plane only once without any overlap. Further details of this data combination technique can be found in the present inventor's earlier cone beam patents, such as U.S. Pat. No. 5,463,666 or U.S. Pat. No. 6,084,937).

The mask consists of a top curve and a bottom curve formed by projecting on to the detector plane the spiral turn above and the spiral turn below the current source position. For a flat detector located at the rotation axis such that the line connecting the source to the detector origin is normal to the detector plane, the equation for the top curve for the spiral scan is given by:

$$v = \frac{h}{2\pi}\tan^{-1}\left(\frac{R}{u}\right)\left(1 + \frac{u^2}{R^2}\right) \quad u \geq 0 \quad (1)$$

$$v = \frac{h}{2\pi}\left[\pi + \tan^{-1}\left(\frac{R}{u}\right)\right]\left(1 + \frac{u^2}{R^2}\right) \quad u < 0$$

where R is the radius of the spiral and h is the distance between adjacent spiral turns (the pitch). The bottom curve is the reflection of the top curve about the origin, i.e. (u,v) ⇒ (−u,−v). The shape of one such spiral mask is shown in FIG. 3. Further detail about the generation and use of data combination masks can be found in my prior cone beam patents, such as U.S. Pat. No. 5,463,666 or U.S. Pat. No. 6,084,937.

The present inventor has realized that although his forenoted U.S. Pat. No. 6,084,937 entitled ADAPTIVE MASK BOUNDARY CORRECTION IN A CONE BEAM IMAGING SYSTEM is intended to reconstruct exact images, in fact there are still image errors. This is because the masking process is only an approximation for limiting calculation of the line integrals intersecting the cone beam image in order to achieve proper data combination. Thus, the reconstruction processing is in fact quasi-exact, i.e., the reconstructed images have artifacts.

It would be desirable to provide a way to easily identify and prevent/correct such image artifacts when performing a simplified image reconstruction processing.

The present inventor has realized one source of image errors comes from "second intersections" between the integration line segments and the mask boundary. More specifically, consider the top mask boundary and the line L illustrated in FIG. 3, where the spiral path which projects onto the mask boundary scans from bottom to top in a clockwise direction. Line L intersects the top mask boundary at 2 points $M_1$ and $M_2$. It then follows that the spiral scan path intersects the integration plane Q defined by the line L and the current source position in the following order: current source position, followed by $M_1$, then followed by $M_2$. Thus the portion of the line that conforms to data combination, i.e. the x-ray data in the angular range bounded by the previous source position below and the subsequent source position above, is the segment to the right of $M_1$. When filtering the cone beam image, it is this segment alone that should be included in the projection operation P(θ), i.e. the line integration operation. However, in the above-mentioned filtered-backprojection reconstruction algorithms (as well as in the above noted linogram technique known for use in Radon space driven reconstruction processing) it is assumed that the entire portion of the line inside the mask is included in the projection operation. That is to say not only the segment to the right of $M_1$ but also the segment to the left of $M_2$ is included in the projection operation. Such unneeded contribution to projection occurs wherever: (1) the line of integration intersects the same mask boundary twice, and (2) the second intersection point lies within the detector. More specifically, for the top and bottom mask boundary, errors are caused by line integration on the line segment to the left and right, respectively, of the second intersection point. It is noted that in the exact Radon space driven reconstruction techniques noted above, these second-intersection contributions were avoided via explicit tabulation for each line integral. Such tabulation is not practical for simplified Radon driven processing (i.e., the linogram technique or for filtered-backprojection processing).

It would be desirable to provide a way to easily identify and prevent/correct such image artifacts due to second intersections with the data combination mask when performing simplified image reconstruction processing.

SUMMARY OF THE INVENTION

A scanning and data acquisition method and apparatus for three dimensional (3D) computerized tomography (CT) imaging of an object, wherein a reconstructed image is developed by calculating reconstruction data along a plurality of line segments L formed in a plurality of sets of 2D cone beam projection data acquired on a detector at a corresponding plurality of source positions about the object. The endpoints of the line segments L formed in the cone beam projection data set acquired at each of the source positions is determined by a data combination mask which is applied to the cone beam projection data set. Line integrals are calculated in the cone beam projection data sets along the line segments to develop a corresponding plurality of processed 2D data sets, each processed 2D data set corresponding to calculation of a first data estimate determined for a given set of the 2D cone beam projection data. 2D correction data for each of the first data estimates is developed by identifying and processing portions of said line segments which are formed by a second intersection with said data combination mask and therefore should not have been used to develop said first data estimates, and processing said identified portions of said line segments to develop the 2D correction data. Each of the first data estimates are then combined with the 2D correction data developed therefore during an image reconstruction process which reconstructs an exact 3D image of the object.

DETAILED DESCRIPTION OF THE INVENTION

Figure 4:
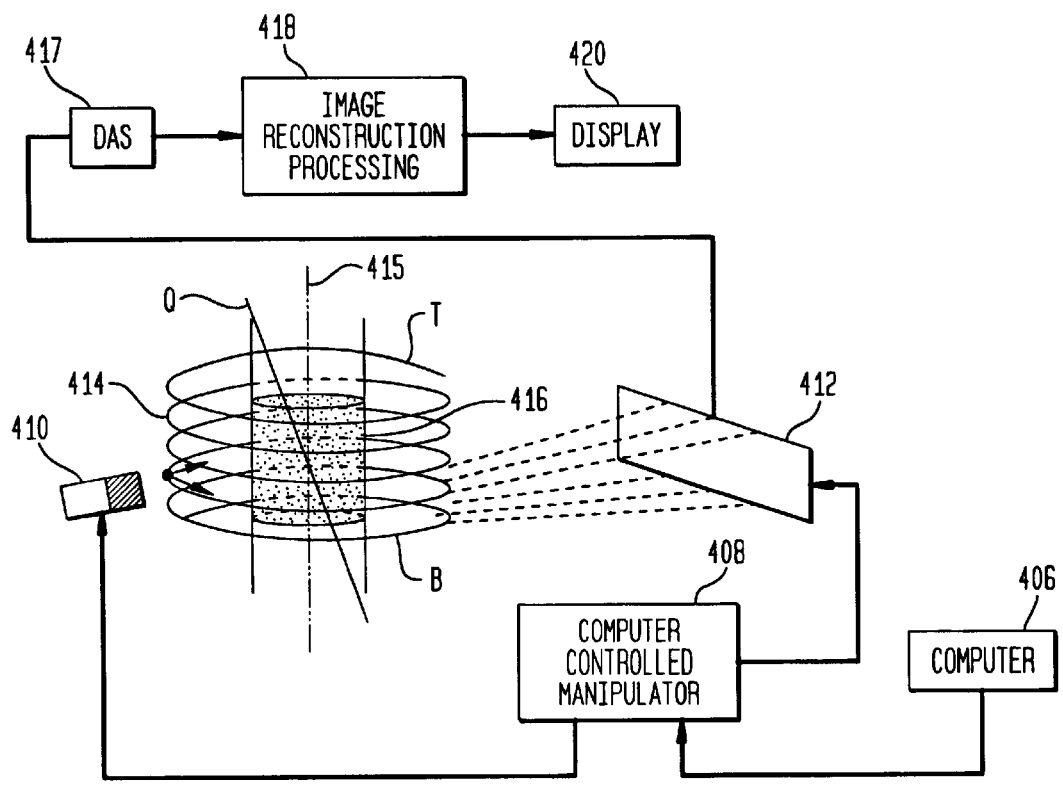
FIG. 4 illustrates a 3D CT imaging apparatus useful for acquiring and processing cone beam data in accordance with the principles of the present invention.

FIG. 4 illustrates a cone beam 3D CT imaging apparatus useful for acquiring and processing acquired cone beam data in accordance with the principles of the present invention. The illustrated imaging apparatus is constructed and operates substantially in accordance with the same principles described in the forenoted U.S. Pat. No. 5,257,183 and uses a masking image reconstruction technique such as described in my forenoted U.S. Pat. Nos. 5,881,123 and 6,084,937, already incorporated herein by reference.

As shown in FIG. 4, a computer controlled manipulator 408, in response to control signals from an appropriately programmed computer 406, cause a source 410 of a cone or pyramid shaped beam of energy (such as x-rays) and a two-dimensional pixelated detector array 412 to cooperate (scan) at a plurality of discreet, sequentially occurring adjacent source positions, along a pre-defined source scanning path. In the illustrated embodiment the scanning path is shown as a spiral scan path 414 centered on a predetermined axis 415 of an object 416, and which proceeds in a clockwise upward spiraling direction. Other types of scan paths that encircle and traverse object 416 can also be used, however, a scan path 414 exhibiting a high degree of symmetry in its parallel projection is preferred.

The only height requirement on the detector is that it should be more than the distance between adjacent turns of a cone beam projection of the spiral scan path 414 onto the detector 412. My U.S. patent application Ser. No. 09/343,770, now abandoned, but which was a continuation-in-part of U.S. patent application Ser. No. 09/274,189, filed Mar. 22, 1999, now U.S. Pat. No. 6,130,930, describes that when only a "region of interest" (ROI, shown as the shaded area of object 416) is to be imaged, providing top and bottom scan path circles at the top and bottom ends, respectively, of the ROI, are not necessary. Thus, a simple continuous spiral scan path 14 that traverses the length of the ROI is all that is needed.

As a result of the source/detector cooperation under control of computer 406 and manipulator 408, at each of the source positions, beams of x-ray energy pass through the field of view of the imaging apparatus, are selectively attenuated by varying energy absorbing densities inside object 416, and a set of cone beam data corresponding to the sensed x-ray energy falling on the elements (pixels) of detector 412 are developed. The sets of cone beam data are then supplied to a data acquisition system (DAS) 417 which, like the previously described portions of FIG. 4, may operate in a fashion well known to those of ordinary skill in this technology for digitizing and storing of the acquired cone beam data.

As described in the present inventor's forenoted U.S. Pat. No. 5,257,183, image reconstruction processing 418 begins by calculating derivative data from the acquired cone beam data, such data being calculated for those portions of integration planes Q which intersect both the scan path and the ROI. One such Q-plane is shown in FIG. 4, and the previously described FIG. 1 illustrating the data combination principle.

When a simplified image reconstruction processing technique is used to develop an image reconstruction of object 416 on a display 420, such as application of the linogram method to a Radon space driven conversion of the derivative data (such as the basic Radon technique known from the forenoted U.S. Pat. No. 5,257,183) or when a FBP technique (such as known from the forenoted U.S. Pat. No. 6,084,937), or the simplified FBP technique (such as known from the forenoted U.S. Pat. No. 5,881,123), the reconstructed image is only quasi-exact and can therefore be considered only an "estimate" image. In either case, the "second intersection" errors must be identified and prevented or corrected to make an exact image reconstruction.

Thus, in accordance with the principles of the present invention, during simplified image reconstruction processing, the "second intersection" errors are identified and prevented or corrected.

In order to identify the source of the "second intersection" errors, the asymptotic behavior of the top mask is derived from Equation (1), so that we obtain:

$$v = \frac{h}{2\pi R} u \quad u \to \infty \quad (2)$$

$$v = \frac{h}{2R^2} u^2 \quad u \to -\infty$$

Figure 5:
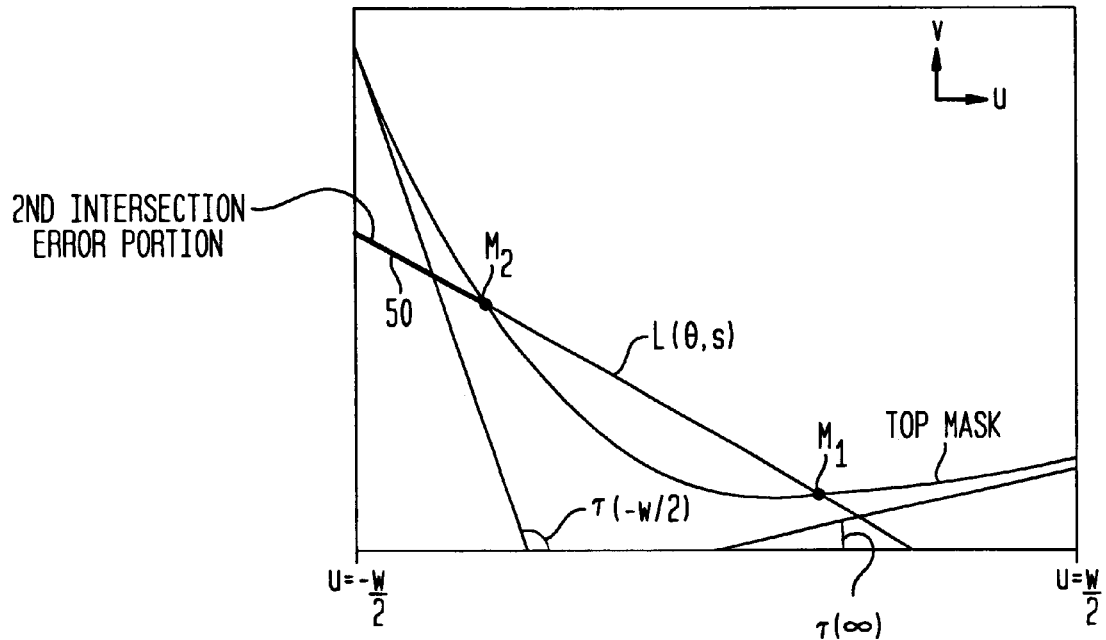
FIGS. 5 and 6 illustrate graphs useful for understanding how to identify the line segments responsible for creating the image artifacts, and which, in accordance with the principles of the present invention, are used for creating correction images.

As shown in FIG. 5, as u ⇒ ∞ the mask approaches a straight line making an angle $\tau(\infty)=\tan^{-1}(h/2\pi R)$ with the u axis, and as u ⇒ −∞ the mask approaches a parabola; Note, $\tau(\infty)$ is also the angle the projected scan path direction t makes with the u axis. It can be shown as a necessary pre-condition to identify those integration lines that intersect the top mask boundary twice, and where the second intersection points lie within the detector, are those lines whose angle θ with the u axis lies within the angular range $A^\perp=[0, \tau(\infty)] \cup [\tau(-W/2), \pi]$, where $\tau(-W/2)$ is the angle the tangent to the mask boundary at the left edge of the detector, U=−W/2, makes with the u axis. Note, in FIG. 5 an exemplary line segment L(θ,s) is shown which has a θ in the second angular range $[\tau(-W/2), \pi]$. Accordingly, the exemplary line segment L(θ,s) has a second intersection error portion 50, which is shown extending to the left of intersection point $M_2$.

In accordance with the principles of the present invention, when using one of the forenoted simplified image reconstruction processing procedures having the forenoted second-intersection error at the upper and lower mask boundaries, a correction procedure for the quasi-exact filtered images (and sometimes referred to herein as "estimated" images), comprises the following steps:

(1) identifying the line segments which intersect the top or bottom mask boundary twice;

(2) developing a 2D correction image using the identified line segments, and (3) subtracting the 2D correction image from the quasi-exact filtered images.

Figure 1A:
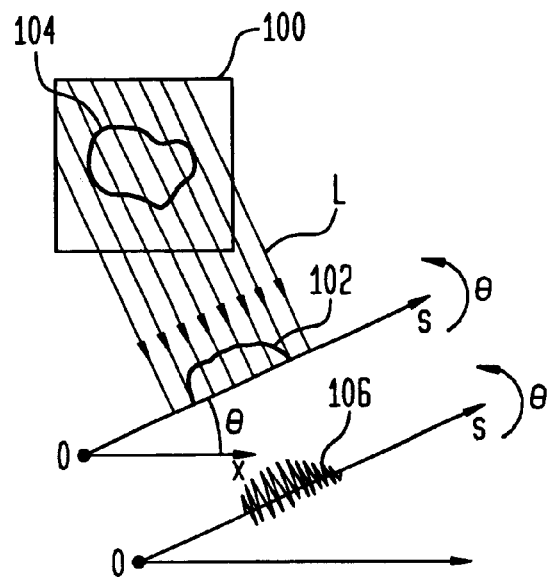
FIGS. 1A and 1B, previously described, illustrate a prior art 3D Filtered BackProjection approach for reconstructing an image.
Figure 1B:
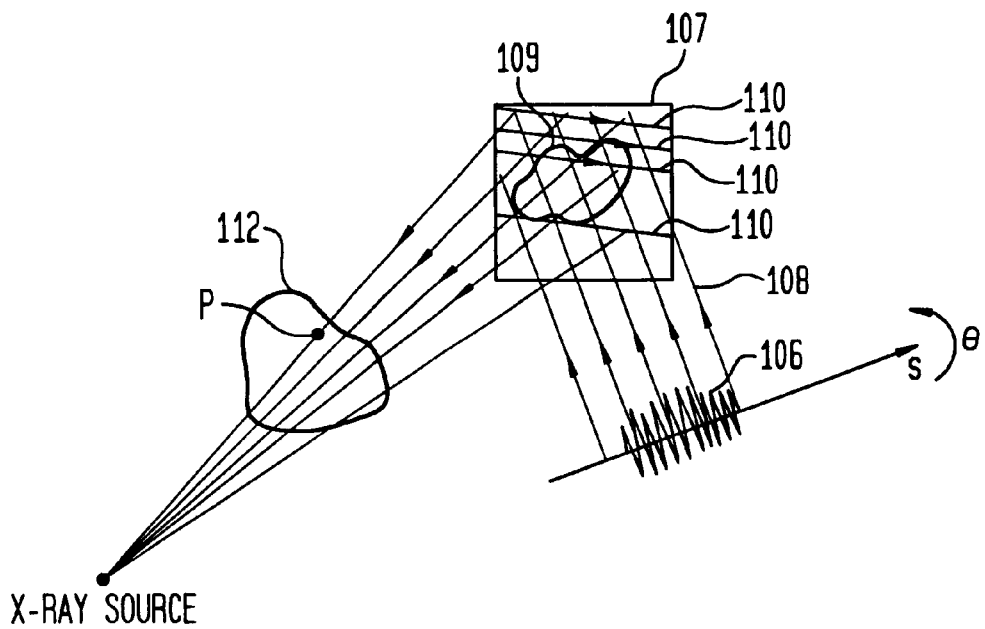
Figure 2:
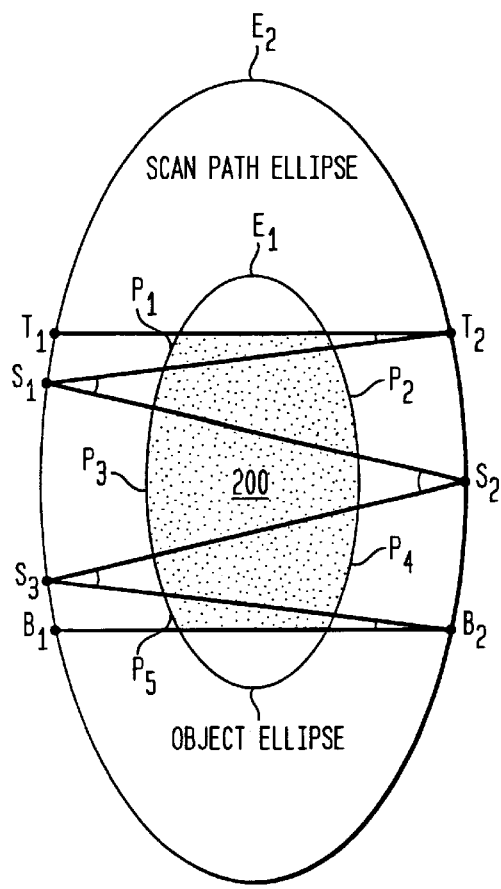
FIGS. 2 and 3, previously described, illustrate the use of a data-combination mask during image reconstruction processing, and how its use can lead to a source of image artifacts.
Figure 3:
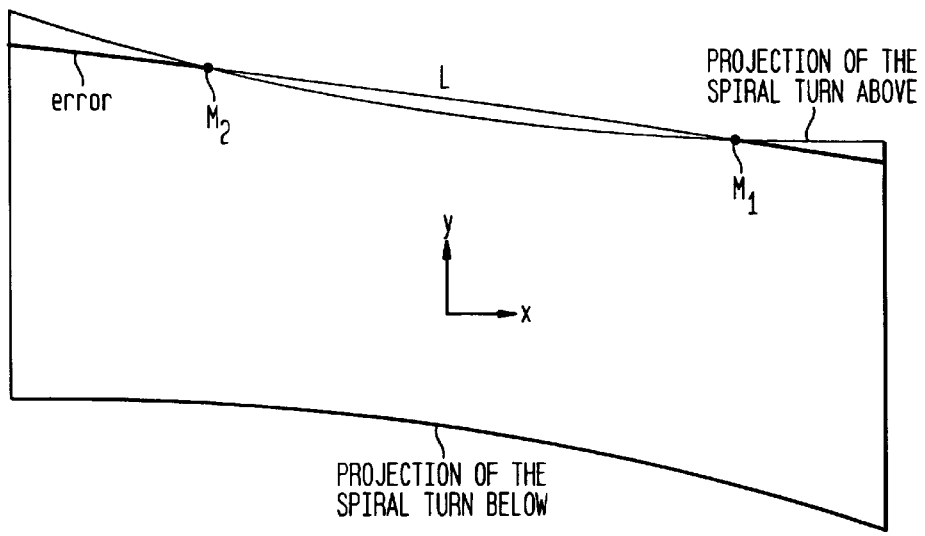

It is noted that step 2, developing a 2D correction image using the identified line segments, can be accomplished by applying the filtering operation $D_tH$ (described in the Background portion of this description and basically comprising the projection/differentiation/2D backprojection operations shown by FIGS. 1A and 1B herein) to the cone beam image along the identified line segments.

Furthermore, it is also noted that the simplified FBP technique described in the present inventor's prior U.S. Pat. No. 5,881,123 can easily be used for forming the quasi-exact image, as follows:

1) applying a mask to each set of 2D cone beam projection data acquired at each source position, thereby forming a masked 2D data set for each source position, 2) ramp filtering the 2D cone beam projection data inside each masked 2D data set, forming ramp filtered 2D data sets, and 3) subjecting the ramp filtered 2D data sets to a weighted 3D backprojection into a 3D space corresponding to a complete field of view of a region of interest (ROI) of the object, thereby reconstructing in the 3D space a 3D image of the ROI in the object.

When using this ramp filtering technique, it is best to subtract the 2D correction image from the quasi-exact ramp filtered 2D data set images, i.e., perform the image subtraction in the 2D domain, rather than the 3D domain.

Figure 6:
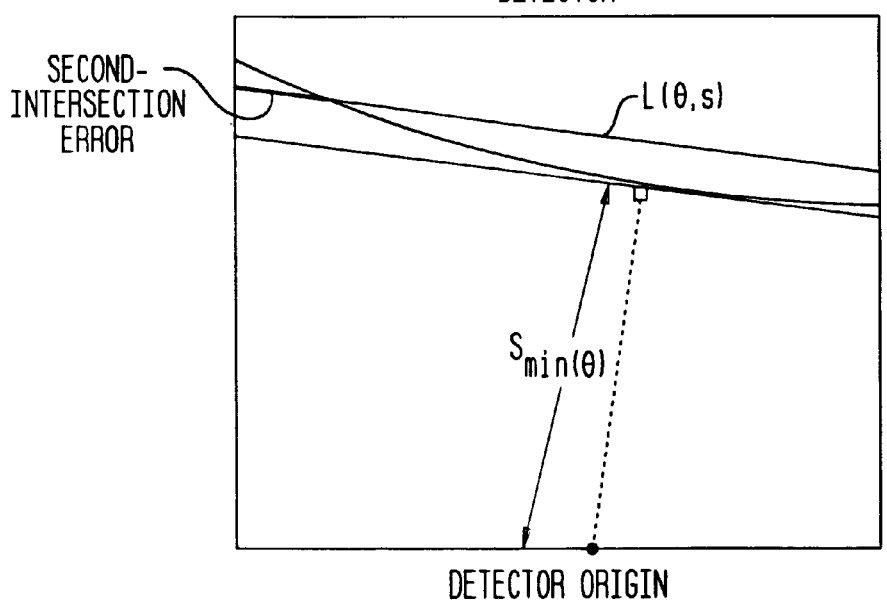

In accordance with another aspect of the present invention, and while referring to FIGS. 5 and 6 (where $L(\theta,s)$ denotes the integration lines as previously defined), it can be shown that line segments having a portion which contribute to the second-intersection errors must satisfy each of the following three conditions:

1. $\theta \epsilon A=[\tau(-W/2)-2, \tau(\infty)+\pi/2]$;
2. $|s|>|s_{min}(\theta)|$, where $L(\theta,s_{min}(\theta))$ is tangential to the top or bottom mask boundary (as shown in FIG. 6); and
3. the line segments which contribute to the second-intersection errors comprise the portion of the line to the left of the second intersection point with the top mask or to the right of the second intersection point with the bottom mask. Of course, in the event that the scan path is scanned in an opposite direction, the affected line segments would be on opposite sides of the identified second intersection point.

Thus, from the above results, out of the entire space of $L(\square,s)$, only a very small percentage of all of the line segments contribute to the second-intersection errors. As a result, these errors can be readily calculated, as noted above by applying the operation DtH to the thus identified portions of the line segments specified by these three conditions. Once identified, these portions are used to develop a correction 2D image, to be combined with (i.e., subtracted) its corresponding quasi-exact 2D image as noted above, and thereby make a more exact 3D reconstructed image.

Thus, there has been shown and described a novel method and apparatus for identifying the source of and for correcting a 2D image created using a simplified image reconstruction processing in a cone beam CT imaging apparatus. Many changes, modifications, variations and other uses and applications of the subject invention will, however, become apparent to those skilled in the art after considering this specification and its accompanying drawings, which disclose preferred embodiments thereof For example, said 2D correction image can be calculated using any of several 2D image creation techniques. Furthermore, the correction image can be combined with the quasi-exact image during the 3D back projection step instead of while the images are still 2D projection images. All such changes, modifications, variations and other uses and applications which do not depart from the teachings herein are deemed to be covered by this patent, which is limited only by the claims which follow as interpreted in light of the foregoing description.

What is claimed is:

1. A method for three dimensional (3D) computerized tomographic (CT) imaging of an object, comprising:

acquiring a plurality of sets of 2D cone beam projection data by irradiating the object with energy from a cone beam source that is directed toward a 2D detector at a corresponding plurality of scan path source positions located about the object;

applying a mask to each set of the 2D cone beam projection data to form a corresponding plurality of masked 2D data sets;

processing line integrals in the 2D cone beam projection data along a plurality of line segments $L(s,\theta)$ having their end points determined by the boundaries of each of the masked 2D data sets to develop a corresponding plurality of processed 2D data sets, each processed 2D data set corresponding to calculation of a first data estimate determined for a given set of the 2D cone beam projection data;

developing 2D correction data for each of the first data estimates by identifying and processing a portion of each of said line segments which is formed by a second intersection with said data combination mask and therefore is not used to develop said first data estimates, and processing said identified portions of said line segments to develop said 2D correction data; and combining each of said first data estimates with the 2D correction data developed therefore during an image reconstruction process which reconstructs an exact 3D image of the object.

2. The method of claim 1, wherein said step which develops said 2D correction data determines line integral derivative data for the 2D cone beam projection data in the masked 2D data sets that lie along only a portion of an identified sub-set of a plurality of line segments $L(s,\theta)$ having their end points bound by the mask in each of the masked 2D data sets, and backprojecting the line integral derivative data into a 2D space along a corresponding backprojection direction ($\theta$), so as to develop a 2D correction image from each of said processed 2D data sets.

3. The method of claim 2, wherein the developing of said 2D correction data comprises calculating line integral derivative data for portions of said line segments $L(s,\theta)$ identified as having two intersections with a top or bottom boundary of the mask, and backprojecting said line integral derivative data into a 2D space to develop said 2D correction data.

4. The method of claim 2, wherein said line segments $L(s,\theta)$ which intersect a top or bottom boundary of the mask twice are identified as those line segments where:

$$\theta \epsilon A=[\tau(-W/2)-\pi/2, \tau(\infty)+\pi/2];$$

and where $|s|>|s_{min}(\theta)|$, where $L(\theta,s_{min}(\theta))$ is tangential to the top or bottom mask boundary.

5. The method of claim 2, wherein those portions of said line segments which intersect the mask twice and are therefore used to develop said 2D correction data comprise those portions of each of the line segments which are inside said masked data set and are positioned subsequent to the second intersection point with the mask.

6. The method of claim 2, wherein said step which develops said first data estimate determines line integral derivative data for the 2D cone beam projection data in the masked 2D data sets that lie along a plurality of line segments $L(s,\theta)$ having their end points bound by the mask in each of the masked 2D data sets, and backprojecting the line integral data into a 2D space along a corresponding backprojection direction ($\theta$), so as to develop a 2D image from each of said processed 2D data sets.

7. The method of claim 2, wherein said step which develops said first data estimate processes the 2D cone beam projection data inside the mask boundaries by Feldcamp ramp filtering of said data along a plurality of parallel lines formed therein.

8. The method of claim 7 wherein said combining step includes subtraction of the 2D correction image from each of said corresponding 2D images, for creating a corrected 2D image.

9. The method of claim 2 wherein said combining step includes weighted 3D backprojection of said corrected 2D image into a common 3D space, thereby reconstructing in said 3D space a corrected 3D image of the object.

10. The method of claim 3 wherein said combining step includes weighted 3D backprojection of said corrected 2D image into a common 3D space, thereby reconstructing in said 3D space a corrected 3D image of the object.

11. The method of claim 9 wherein before said 3D backprojection step, said 2D corrected image is filtered.

12. Apparatus for three dimensional (3D) computerized tomographic (CT) imaging of an object, comprising:

a cone beam source for applying radiation energy to at least a portion of the object;

a 2D area detector for detecting radiation energy;

means for defining a source scanning trajectory as a scan path traversed by the source;

a manipulator for causing the cone beam source, fixed relative to an area detector with both source and detector movably positioned relative to the object, to scan about the object at a plurality of source positions in a direction along the scan path to cause said area detector to acquire a set of 2D cone beam projection data at each of said source positions;

a masking means for applying a mask to each set of the acquired 2D projection data to form masked data sets;

estimating means for processing line integrals in the 2D cone beam projection data along a plurality of line segments $L(s,\theta)$ having their end points determined by the boundaries of each of the masked 2D data sets to develop a corresponding plurality of processed 2D data sets, each processed 2D data set corresponding to calculation of a first data estimate determined for a given set of the 2D cone beam projection data;

a correction processor means for developing 2D correction data for each of the first data estimates by identifying and processing a portion of each of said line segments which is formed by a second intersection with said data combination mask and therefore is not used to develop said first data estimates, and processing said identified portions of said line segments to develop said 2D correction data; and combining means for combining each estimated 2D data set and the 2D correction data developed therefore during an image reconstruction process which reconstructs an exact 3D image of the object.

13. The apparatus of claim 12, wherein the estimating means comprises a ramp filter processor for ramp filtering the 2D cone beam projection data inside the mask boundaries of each masked 2D data along a plurality of parallel lines formed therein.

* * * * *